United States Patent
Al-Shafei et al.

(10) Patent No.: US 11,066,605 B2
(45) Date of Patent: Jul. 20, 2021

(54) SYSTEMS AND METHODS FOR CATALYTIC UPGRADING OF VACUUM RESIDUE TO DISTILLATE FRACTIONS AND OLEFINS

(71) Applicant: SAUDI ARABIAN OIL COMPANY, Dhahran (SA)

(72) Inventors: Emad Naji Al-Shafei, Dhahran (SA); Mohamed Al-Bahar, Dhahran (SA); Ali Nader Al-Jishi, Dhahran (SA); Ki-Hyouk Choi, Dhahran (SA); Mohammad Al-Jishi, Dhahran (SA); Ali Al-Nasir, Dhahran (SA)

(73) Assignee: SAUDI ARABIAN OIL COMPANY, Dhahran (SA)

(*) Notice: Subject to any disclaimer, the term of this patent is extended or adjusted under 35 U.S.C. 154(b) by 0 days.

(21) Appl. No.: 16/681,513

(22) Filed: Nov. 12, 2019

(65) Prior Publication Data

US 2021/0139790 A1 May 13, 2021

(51) Int. Cl.
*C07C 4/00* (2006.01)
*C10G 11/05* (2006.01)
(Continued)

(52) U.S. Cl.
CPC ............ *C10G 11/05* (2013.01); *B01J 8/0278* (2013.01); *B01J 8/0285* (2013.01); *B01J 29/40* (2013.01);
(Continued)

(58) Field of Classification Search
CPC ...... B01J 29/40; B01J 35/023; B01J 35/1019; B01J 35/1061; B01J 2029/062;
(Continued)

(56) References Cited

U.S. PATENT DOCUMENTS

| 3,954,600 A | 5/1976 | Gladrow et al. |
| 4,172,816 A | 10/1979 | Boteanu et al. |

(Continued)

FOREIGN PATENT DOCUMENTS

| CN | 100537714 C | 9/2009 |
| CN | 108264935 A | 7/2018 |

(Continued)

OTHER PUBLICATIONS

Galadima, A. et. al, Hydrocracking catalysts based on hierarchical zeolites: A recent progress, Journal of Industrial and Engineering Chemistry, 2018, 265-280.
(Continued)

*Primary Examiner* — Sharon Pregler
(74) *Attorney, Agent, or Firm* — Bracewell LLP; Constance G. Rhebergen; Kevin R. Tamm

(57) ABSTRACT

Systems and methods for upgrading a heavy oil feed to a light product comprising distillate fractions and olefins, the method including combining a heavy oil feed with a naphtha-based cracking additive to produce a mixed heavy oil feed; heating the mixed heavy oil feed with a nano-zeolite catalyst to effect catalytic upgrading of the mixed heavy oil feed to produce lighter distillate fractions and olefins in an upgraded product; and separating the lighter distillate fractions from the olefins.

21 Claims, 1 Drawing Sheet

(51) Int. Cl.

| | | |
|---|---|---|
| *B01J 29/40* | (2006.01) | |
| *B01J 35/00* | (2006.01) | |
| *B01J 29/90* | (2006.01) | |
| *B01J 38/12* | (2006.01) | |
| *B01J 8/02* | (2006.01) | |

(52) U.S. Cl.
CPC .......... *B01J 29/90* (2013.01); *B01J 35/0013* (2013.01); *B01J 38/12* (2013.01); *C07C 4/00* (2013.01); *C07C 2521/04* (2013.01); *C07C 2521/08* (2013.01); *C07C 2521/12* (2013.01); *C07C 2529/40* (2013.01); *C10G 2300/1044* (2013.01); *C10G 2300/1077* (2013.01); *C10G 2300/301* (2013.01); *C10G 2300/308* (2013.01); *C10G 2300/70* (2013.01); *C10G 2400/04* (2013.01); *C10G 2400/06* (2013.01); *C10G 2400/08* (2013.01); *C10G 2400/20* (2013.01)

(58) Field of Classification Search
CPC .......... C10G 9/36; C10G 11/05; C10G 11/18; C10G 55/04; C10G 1/10; C10G 69/06; C10G 21/003; C10G 69/04; C10G 47/20; C10G 11/00; C10G 1/002; C10G 51/06; C10G 67/0463; C10G 51/02; C10G 9/005; C10G 11/04; C10G 11/185; C10G 11/20; C10G 19/00
See application file for complete search history.

(56) References Cited

U.S. PATENT DOCUMENTS

| | | | |
|---|---|---|---|
| 4,340,465 | A | 7/1982 | Miller et al. |
| 4,976,847 | A | 12/1990 | Maxwell et al. |
| 4,980,053 | A | 12/1990 | Li et al. |
| 5,278,114 | A | 1/1994 | Wielers et al. |
| 5,326,465 | A | 7/1994 | Yongqing et al. |
| 6,210,562 | B1 | 4/2001 | Xie et al. |
| 6,211,104 | B1 | 4/2001 | Shi et al. |
| 6,420,621 | B2 | 7/2002 | Sha et al. |
| 6,743,961 | B2 | 5/2004 | Powers |
| 7,033,486 | B2 | 4/2006 | Gorbaty et al. |
| 7,404,889 | B1 | 7/2008 | Powers |
| 7,550,642 | B2 | 6/2009 | Powers |
| 8,137,534 | B2 | 3/2012 | Upson et al. |
| 8,696,887 | B2 | 4/2014 | Xu et al. |
| 9,212,318 | B2 | 12/2015 | Narayanaswamy et al. |
| 9,228,140 | B2 | 1/2016 | Abba et al. |
| 9,284,497 | B2 | 3/2016 | Bourane et al. |
| 9,284,502 | B2 | 3/2016 | Bourane et al. |
| 9,382,486 | B2 | 7/2016 | Bourane et al. |
| 9,428,695 | B2 | 8/2016 | Narayanaswamy et al. |
| 9,670,418 | B2 | 6/2017 | Schmidt et al. |
| 10,407,311 | B2 * | 9/2019 | Ding .................... B01J 35/0066 |
| 2003/0181323 | A1 | 9/2003 | Le Van Mao |
| 2004/0004022 | A1 | 1/2004 | Stell et al. |
| 2004/0054247 | A1 | 3/2004 | Powers |
| 2005/0209495 | A1 | 9/2005 | McCoy et al. |
| 2008/0093261 | A1 | 4/2008 | Powers |
| 2011/0000819 | A1 | 1/2011 | Keusenkothen |
| 2016/0333280 | A1 | 11/2016 | Subramani et al. |
| 2017/0166819 | A1 | 6/2017 | Choi et al. |
| 2017/0369397 | A1 | 12/2017 | Al-Herz et al. |
| 2018/0002609 | A1 | 1/2018 | Narayanaswamy et al. |
| 2018/0216009 | A1 | 8/2018 | Narayanaswamy et al. |
| 2018/0333708 | A1 | 11/2018 | Ding et al. |
| 2018/0334390 | A1 | 11/2018 | Ding et al. |
| 2019/0023997 | A1 * | 1/2019 | Sundaram .............. C10G 51/06 |

FOREIGN PATENT DOCUMENTS

| | | |
|---|---|---|
| DE | 152356 A1 | 11/1981 |
| WO | 0132806 A1 | 5/2001 |

OTHER PUBLICATIONS

Genquan, et al.; Research and Commerical Application of CPP Technology for Producing Light Olefins from Heavy Oil; China Petroleum Processing and Petrochemical Technology; Sep. 30, 2013, pp. 7-12; vol. 15, No. 3.

U.S. Appl. No. 16/681,517, "Systems and Methods for Catalytic Upgrading of Vacuum Residue to Distillate Fractions and Olefins with Steam", filed Nov. 12, 2019.

International Search Report and Written Opinion, PCT Application No. PCT/US2020/059815, dated Feb. 10, 2021.

International Search Report and Written Opinion, PCT Application No. PCT/US2020/059816, dated Feb. 15, 2021.

* cited by examiner

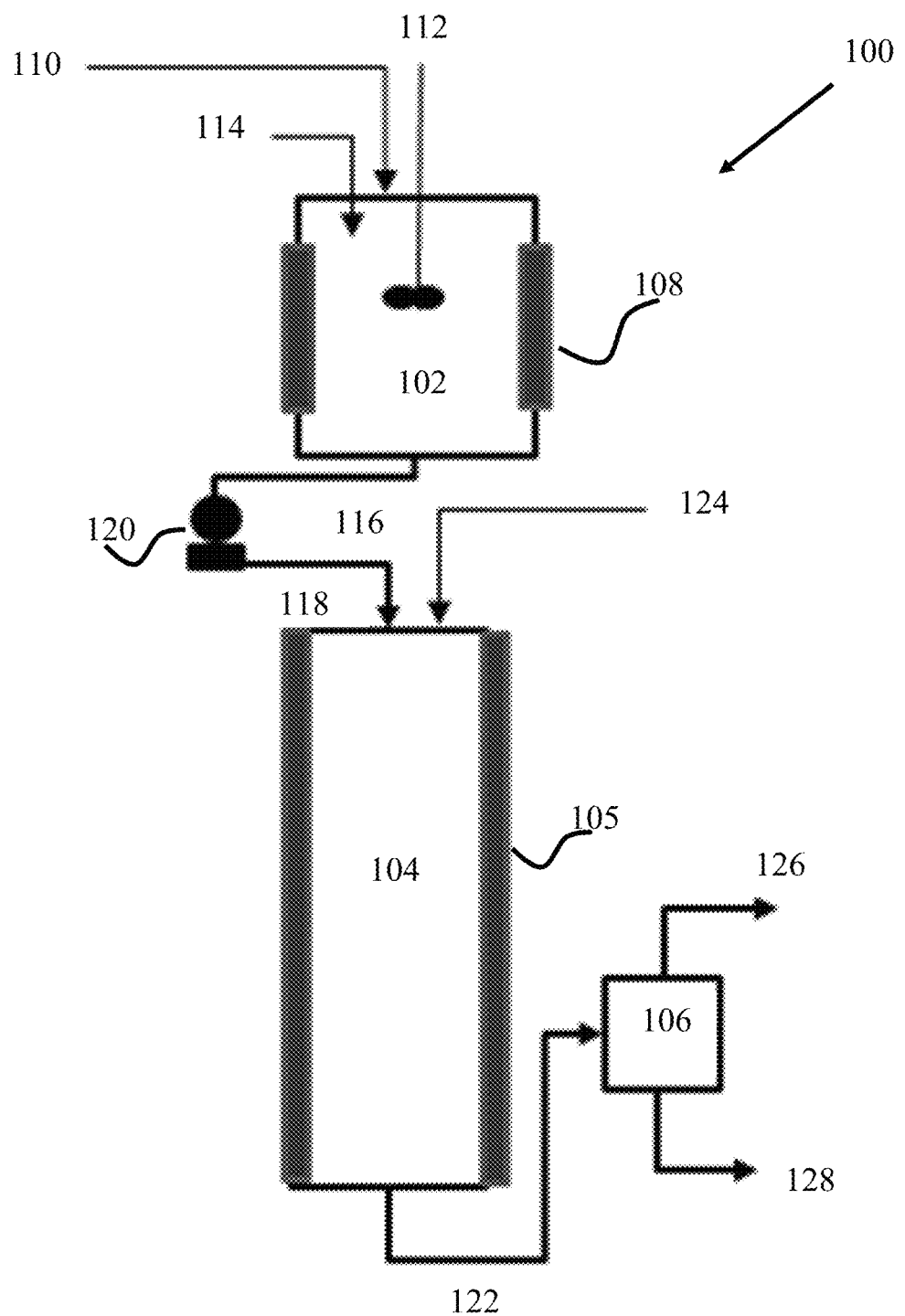

SYSTEMS AND METHODS FOR CATALYTIC UPGRADING OF VACUUM RESIDUE TO DISTILLATE FRACTIONS AND OLEFINS

BACKGROUND

Field

The present disclosure relates to systems and methods for upgrading vacuum residue in addition to or alternative to heavy vacuum gas oil to distillate fractions and olefins. Specifically, the disclosure presents high temperature catalytic upgrading systems and methods for upgrading vacuum residues to distillate fractions and olefins applying a naphtha-based cracking additive.

Description of the Related Art

Direct upgrading of de-metalized and de-asphalted oils from vacuum residue and heavy gas oil is a problematic and challenging process for integrated refineries, preventing production of highly valuable products such as olefins. Hydrocracker processes are important for the production of clean fuels in refineries, and full conversions of vacuum gas oil (VGO) mixed with some de-metalized oil (DMO) has been achieved. However, limited yields of highly valuable olefins are obtained. Thermal cracking based on carbon rejection techniques in coker units is utilized to convert heavy feedstocks, but low olefin yields are usually obtained, accompanied by high yields of coke. Conventional fluidized catalytic cracking (FCC) processes involve a catalytic pyrolysis process, and are mainly applied for converting VGO. FCC is not designed to be directly used to convert vacuum residue feedstocks. Moreover, a high catalyst to oil ratio is required.

Converting vacuum residue to more valuable products should be considered by refineries so that low value products can be turned into more valuable products for petrochemical industries. State of the art technologies for processing vacuum residues include using carbon rejection or hydrogen addition processes. Carbon rejection is a useful process, but produces low content of olefins and allows for coke formation. Hydrocracking processes provide for full conversion of heavy feedstocks to various clean fuels. However, limited yield of olefin gas is produced from the upgrading processes of VGO, DAO, and DMO.

Technologies such as high-severity fluidized catalytic cracking (HS-FCC) and deep catalytic cracking (DCC) are processes for vacuum gas oil conversion, producing olefins and distillate fractions. Yet, these technologies show limited conversion of vacuum residue feedstocks and are not utilized for such types of residue directly. Furthermore, steam cracking units have not been applied in any commercial petrochemical plant to convert vacuum residue feedstocks due to a high rate of coking from heavy molecules and low yields of olefins.

Several technologies have attempted catalytic cracking using various catalysts without the introduction of any hydrogen to the system for the conversion of heavy residue feedstocks to more valuable products. Overall, most state of the art technology discloses FCC reactor configurations and several catalysts in order to conduct upgrading of heavy residues. However, these processes require micro-sized zeolite crystals modified with a variety of additives and metals. Also, high catalyst to oil ratios are used, despite steam introduction to FCC reactors.

Zeolite catalysts play an important role in any hydrocarbon catalytic cracking process despite the different preparation methods, modifications, and reactor configurations. Conversion of heavy vacuum residue and heavy vacuum gas oil feedstocks is challenging, and integrated refineries face multiple difficulties utilizing and converting such heavy feedstocks. Converting these feedstocks by a hydrocracking unit will produce low olefin yields with high yields of clean fuel.

Performing thermal cracking on vacuum residue feedstocks in coker units produces low olefin yields alongside distillate products. In addition, the products are accompanied by large amounts of coke. Steam cracking units are usually utilized for chemical conversion of naphtha and gas oil, but have not been used for vacuum residue upgrading due to the low yield of olefins and the high rate of coking. In addition, there is no commercial process based on FCC to be utilized for upgrading vacuum residue feedstocks, which are still considered to be challenging feeds to produce olefins and distillate fractions.

SUMMARY

Applicant has recognized a need for systems and methods that upgrade de-metalized and de-asphalted oil from vacuum residue in addition to or alternative to heavy vacuum gas oil to produce valuable distillate fractions and olefins. In certain embodiments disclosed here, high temperature catalytic upgrading systems and processes are disclosed for heavy vacuum gas oil and for de-metalized and de-asphalted oils from vacuum residues, which produce valuable distillate fractions and olefins. Embodiments of systems and methods show upgrading heavy vacuum gas oils (optionally in addition to or alternative to light vacuum gas oil (LVGO)) and vacuum residues by mixing the heavy vacuum gas oils or vacuum residues with straight run naphtha, which is used as a cracking additive. Disclosed embodiments enhance catalyst activity and help effectively crack heavier molecules in a heavy feed either on the external surfaces or the inner pores of nano-zeolite catalyst crystals. Certain embodiments allow for advantageously increasing the production of distillate fractions (about 30-55 wt. % of an upgraded hydrocarbon product) and allow for advantageously increasing yields of olefins (about 25-40 wt. % of an upgraded hydrocarbon product) from vacuum residue and heavy vacuum gas oil feedstocks.

Certain systems and methods apply the use of a fixed bed reactor loaded with nano-zeolite catalysts. Systems can include the use of multiple bed reactor systems with a swing reactor concept wherein one reactor is removed from service for regeneration and a freshly regenerated reactor is simultaneously returned to service. In addition, straight run naphtha is used as a cracking additive to enhance the cracking activity of heavy molecules leading to the production of distillate fractions alongside lighter valuable olefins. Systems and methods are advantageous in utilizing heavy low value feedstocks to produce more valuable products.

Suitable cracking additives include, but are not limited to, any one of or any combination of straight run naphtha with a boiling point range between about 200° F. to about 400° F., straight run naphtha with a boiling point range between about 315° F. to about 400° F., straight run naphtha with a boiling point range between about 250° F. to about 400° F., straight run naphtha with a boiling point range between about 250° F. to about 350° F., straight run kerosene with a boiling point range between about 400° F. to about 500° F., a mixture of naphtha with a boiling point range between about 315° F. to about 400° F. and kerosene with a boiling point range between about 400° F. to about 500° F., for example about 50 wt. % naphtha and about 50 wt. % kerosene, or about 75 wt. % naphtha and about 25 wt. % kerosene, or about 25 wt. % naphtha and about 75 wt. % kerosene. These feed additives can be used to enhance the production of olefins and distillate fractions from heavy vacuum feedstocks and gas oils.

With the direct catalytic upgrading technology described here, efficient conversion of DMO, DAO, heavy vacuum gas oil (HVGO), and other heavy vacuum gas residues to olefin and distillate fractions is achievable. Mixing these heavy feedstocks with a diluent or cracking additive beforehand allows for larger quantities of distillate fractions and olefins to be produced.

Nano-zeolite crystals with low catalyst to oil ratio were used to overcome certain challenges associated with the conversion of heavy vacuum residue feedstocks for the production of high yields of light olefins and distillate fractions compared to established carbon rejection and hydrocracking processes. Vacuum residue feedstock is a difficult feedstock to handle and has not been utilized in the production of valuable chemicals such as BTX (benzene, toluene, and xylene) and light olefins due the low yield of these chemical that is obtained with state of the art technologies. In addition, vacuum residue has not been used as a feedstock for steam cracking units. Certain embodiments overcome the upgrading limitations of vacuum residues such as DMO, DAO, and HVGO feedstocks. Embodiments of systems and methods are designed to be operated at atmospheric pressure or greater without or in the absence of a supply of hydrogen. Additionally, embodiments of the catalytic upgrading process are designed to operate without or in the absence of steam. The catalytic upgrading systems and methods unexpectedly utilize lower catalyst to oil ratios than conventional FCC technology to convert vacuum residues to distillate fractions and olefins.

Residue from vacuum distillation contains the major portion of the asphaltene fraction of processed crude oil. Vacuum residue contains high concentrations of Conradson Carbon residue and metal components. It also contains high levels of heteroatoms such as nitrogen and sulfur. Vacuum residue generally cannot be used as feedstock for catalytic cracking because its high metal content leads to catalyst deactivation. Solvent de-asphalting of vacuum residue produces what is referred to as a DAO or DMO fraction of relatively low metal content and a heavier fraction containing the rest of the metals. Factors affecting this process are: vacuum residue and solvent quality, solvent/charge ratio (S/C), temperature and pressure.

The catalytic upgrading systems and methods can be operated for longer reaction cycles with slower deactivation rates than FCC technologies for converting vacuum residues to distillate fractions and olefins. One catalyst used in the catalytic upgrading process, for example, is extruded nano ZSM-5 zeolite crystal with an alumina binder. Other suitable catalyst materials include nano-zeolite catalyst material of one-dimensional or three-dimensional structures with medium pores and large pores (10-12 atoms) to uptake heavy hydrocarbon molecule components, including heavy residues and gas oils. In some embodiments, the nano-zeolite crystals are synthesized using a silica source that is either tetraethylorthosilicate (TEOS), silica gel, colloidal silica 20 wt. %, colloidal silica 30 wt. %, colloidal silica 40 wt. %, or fumed silica. Furthermore, tetrapropylammonium hydroxide can be used as a template during crystallization and formulation of suitable nano ZSM-5 crystals. A cracking additive such as straight run naphtha is used in this process to assist heavy molecules breaking catalytically in order to produce distillate fractions and olefins.

Catalytic upgrading processes for vacuum residue can be carried out by mixing a heavy vacuum residue feed with a cracking additive, for example, straight run naphtha at between about 10 wt. % to about 20 wt. % of a mixed feed of heavy vacuum residue (in addition or alternative to gas oil) and the cracking additive. This allows nano-zeolite catalysts to be more active as more hydrogen radicals became available, which assists in achieving higher cracking activity on the external and internal acidic sites of the nano-zeolite catalyst.

With the cracking additive it is believed, without being bound by any theory or practice, that the internal pores of nano-zeolite catalysts produce intermediate by-product molecules. Then, these intermediate by-products react again, which increases the reactivity of the catalyst to assist in increasing the reaction rate of vacuum residue feedstock cracking mostly via external pores of the catalyst. As a result of the catalytic upgrading process conversion rates were improved without using steam. Distillate fractions in the range of 30-55 wt. % and high value of olefins gas in the range of 25-40 wt. % from vacuum residue feedstocks were obtained in upgraded hydrocarbon products.

The catalytic upgrading systems and methods convert, for example, multiple types of vacuum residues and HVGO to produce distillate fractions, olefins, and hydrogen. The olefins produced from vacuum residue are in the range 25-40 wt. % of a catalytically upgraded product. Embodiments advantageously utilize a surprisingly and unexpectedly lower catalyst to oil ratio than traditional FCC processes.

Thus, disclosed here is a method for upgrading a heavy oil feed to a light product comprising distillate fractions and olefins, the method including combining a heavy oil feed with a naphtha-based cracking additive to produce a mixed heavy oil feed; heating the mixed heavy oil feed with a nano-zeolite catalyst to effect catalytic upgrading of the mixed heavy oil feed to produce lighter distillate fractions and olefins in an upgraded product, the upgraded product including at least about 20 wt. % olefins; and separating the lighter distillate fractions from the olefins. In some embodiments, the heavy oil feed has an American Petroleum Institute (API) gravity between about 5 and about 22. In other embodiments, the heavy oil feed is selected from the group consisting of: de-asphalted oil, de-metalized oil, heavy vacuum gas oil, and combinations thereof. Still in other embodiments, the naphtha-based cracking additive comprises straight run naphtha with an API gravity from about 40 to about 77 and a boiling point range from between about 200° F. to 500° F.

In certain other embodiments of the method, the naphtha-based cracking additive includes at least one component selected from the group consisting of: straight run naphtha with a boiling point range between about 200° F. to about 400° F., and straight run kerosene with a boiling point range between about 400° F. to about 500° F. Still in other embodiments, the naphtha-based cracking additive is between about 5 wt. % to about 30 wt. % of the mixed heavy oil feed. In certain other embodiments, the naphtha-based cracking additive is between about 10 wt. % to about 25 wt. % of the mixed heavy oil feed. In some embodiments, the step of heating is carried out at between about 575° C. to about 650° C. for between about 2 hours to about 6 hours. Still in some other embodiments, the step of heating is carried out at between about 590° C. to about 610° C. for between about 3 hours to about 4 hours. In certain embodiments, the nano-zeolite catalyst comprises a nano ZSM-5 silica/alumina zeolite with a silica:alumina molar ratio between about 20 to about 250 with zeolite crystals sized from about 50 to about 350 nm.

In certain other embodiments, the nano-zeolite catalyst comprises a nano-zeolite catalyst material of one-dimensional or three-dimensional structure with medium pores and large pores operable to uptake heavy hydrocarbon molecule components from the mixed heavy oil feed. Still in other embodiments, the lighter distillate fractions include at least one component selected from the group consisting of: naphtha, kerosene, diesel, and fuel oil. In some embodiments of the method, the olefins include at least one component selected from the group consisting of: ethylene, propylene, and butenes. Still in other embodiments, the method includes the step of regenerating the nano-zeolite catalyst to remove coke after the step of heating, the step of regenerating comprising heating the nano-zeolite catalyst under air at between about 650° C. to about 750° C. for between about 3 hours to about 5 hours.

Certain embodiments include the step of measuring $CO_2$ content to determine completion of the step of regenerating the nano-zeolite catalyst. Still in other embodiments, the step of combining includes stirring the heavy oil feed and naphtha-based cracking additive with a stirrer at between about 50 rpm and about 1500 rpm for between about 1 hour and about 2 hours. In certain other embodiments, the upgraded product comprises between about 5-10 wt. % hydrogen gas, about 20-40 wt. % olefin gas, and about 28-55 wt. % lighter distillate fractions. In still yet other embodiments, the step of heating is carried out without hydrogen addition and without steam addition. In certain other embodiments, the nano-zeolite catalyst to mixed heavy oil feed weight ratio is between about 0.5:2 to about 0.5:24.

Additionally disclosed here is a system to carry out the various method step, the system including a thermal mixing unit with a stirrer to adapted for the step of combining; a catalytic upgrading unit in fluid communication with the thermal mixing unit and adapted for the step of heating; and a gas-liquid separator unit adapted for the separating step. In some embodiments, the system includes a heated pump and a heated line between the thermal mixing unit and the catalytic upgrading unit. Still in yet other embodiments, the catalytic upgrading unit is in fluid communication with a nitrogen feed and an air feed for a step of regenerating the nano-zeolite catalyst to remove coke. In certain other embodiments, the catalytic upgrading unit comprises a fixed bed reactor with the nano-zeolite catalyst disposed in the fixed bed reactor.

BRIEF DESCRIPTION OF THE DRAWINGS

These and other features, aspects, and advantages of the present disclosure will become better understood with regard to the following descriptions, claims, and accompanying drawings. It is to be noted, however, that the drawings illustrate only several embodiments of the disclosure and are therefore not to be considered limiting of the disclosure's scope as it can admit to other equally effective embodiments.

FIG. 1 is a schematic representing a system and process for catalytic upgrading of heavy vacuum residues in addition to or alternative to heavy vacuum gas oil using a nano-zeolite catalyst and cracking additive without steam or hydrogen addition.

DETAILED DESCRIPTION

So that the manner in which the features and advantages of the embodiments of systems and methods that provide heavy vacuum residue in addition to or alternative to heavy gas oil catalytic upgrading, as well as others, which will become apparent, may be understood in more detail, a more particular description of the embodiments of the present disclosure briefly summarized previously may be had by reference to the embodiments thereof, which are illustrated in the appended drawings, and which form a part of this specification. It is to be noted, however, that the drawings illustrate only various embodiments of the disclosure and are therefore not to be considered limiting of the present disclosure's scope, as it may include other effective embodiments as well.

Referring now to FIG. 1, a schematic is shown demonstrating an embodiment of a system and method for catalytic upgrading. Catalytic upgrading system 100 includes a thermal feed mixing unit 102, a catalytic upgrading unit 104, and a gas-liquid separator unit 106. Thermal feed mixing unit 102 includes a wall heater 108, which in some embodiments is set to between about 80° C. to about 130° C. to heat a mixed feed in thermal feed mixing unit 102. In one example embodiment of catalytic upgrading system 100, thermal feed mixing unit 102 receives a pre-heated de-metalized oil, de-asphalted oil, heavy vacuum gas oil, or combined feed thereof at about between about 80° C. to about 130° C. via feed stream 110. Stirrer 112 is stirred at a speed between about 50 rpm to about 200 rpm. During or after feed addition, a cracking additive such as straight run naphtha is introduced via cracking additive stream 114. In some embodiments, the cracking additive stream such as straight run naphtha is added at between about 5 wt. % to about 30 wt. % of the total mixed feed, or between about 10 wt. % to about 20 wt. % of the total mixed feed, such as a DMO feed.

Once a heavy vacuum residue feed in addition to or alternative to a heavy vacuum gas oil feed has been added via feed stream 110 into thermal feed mixing unit 102 with cracking additive from cracking additive stream 114, then the stirring speed of stirrer 112 is increased to between about 200 rpm and about 500 rpm for between about 1 to about 2 hours to ensure mixing of the heavy feed such as DMO with the cracking additive prior to feeding the mixture to catalytic upgrading unit 104 via heated lines 116, 118 utilizing heated feed pump 120.

Catalytic upgrading unit 104 in some embodiments applies two heating stages to upgrade a heavy feed received from heated line 118. In a first catalytic upgrading stage, the catalytic upgrading unit 104 is operated at a temperature between about 575° C. to about 650° C. for vacuum residue in addition to or alternative to heavy gas oil upgrading. In a second stage for catalytic regeneration, catalytic upgrading unit 104 operates at between about 650° C. to about 750° C. to regenerate nano-zeolite catalyst to remove any accumulated coke under air and/or oxygen.

For example, in the first catalytic upgrading stage, a heated de-metalized oil feed or a heavy vacuum gas oil feed and cracking additive mixture mixed at a temperature between about 80° C. to about 130° C. in thermal feed mixing unit 102 is sent to heated feed pump 120 via preheated line 116. Heated feed pump 120 can operate in some embodiments at between about 100° C. to about 130° C. and injects the mixture of feedstock and cracking additive to catalytic upgrading unit 104 via preheated line 118, which can be heated to between about 150° C. to about 200° C.

The flow of the heated feed pump 120 is adjusted to operate at a liquid hourly space velocity (LHSV) of about 0.1 to about 20 $h^{-1}$, preferably between about 0.25 $h^{-1}$ to about 5 In some embodiments, a catalyst diluent such as silica carbide or similar is disposed proximate the top of a nano-zeolite catalyst bed in catalytic upgrading unit 104 to ensure appropriate heat transfer to the feed mixture prior to coming into contact with the catalyst disposed throughout catalytic upgrading unit 104. One or more catalyst beds with one or more types of catalyst can be applied. Catalytic upgrading reactor 104 is charged with a formulated catalyst including extruded nano ZSM-5 zeolite and alumina binder between about 20 wt. % to about 70 wt. %. The silica/alumina molar ratio of nano ZSM-5 zeolite is in the range of between about 20 to about 250. The nano ZSM-5 zeolite crystals range in size from about 50 nm to about 350 nm.

In some embodiments, the nano ZSM-5 zeolite is synthesized from a silica source which includes tetraethylorthosilicate (TEOS), silica gel, colloidal silica 30 wt. %, colloidal silica 40 wt. %, fumed silica, or combinations thereof. Also, a zeolite template can be applied, which is one embodiment is tetrapropylammonium hydroxide.

In the first catalytic upgrading stage, catalytic upgrading unit 104 temperature is set between about 575° C. to about 650° C., or between about 590° C. to about 610° C., or at about 600° C. prior to receiving the feedstock for upgrading. Heating elements 105 control heating and the heating rate of catalytic upgrading unit 104 during both the upgrading and catalyst regeneration processes described. The products of catalytic upgrading unit 104 include liquid and gas which are evacuated via line 122 in order to be sent to the gas-liquid separator unit 106. The gas products include olefins, hydrogen, methane, ethane, propane, n-butane, i-butane, and other gases. The liquid product includes distillate fractions upgraded from a vacuum residue or HVGO input and a cracker additive feedstock.

In some embodiments, the upgrading process of vacuum residue feed stock, such as DAO or DMO, in addition to or alternative to heavy vacuum gas oil can be run for between about 2 to about 6 hours, preferably for between about 3 to about 4 hours. Once liquid and gas phase products have been evacuated via line 122, heated feed pump 120 is deactivated, preheated line 118 is closed, and a catalyst regeneration process begins in catalytic upgrading unit 104.

The catalyst in catalyst upgrading unit 104, for example one or more catalyst beds including one or more types of catalysts, is regenerated to remove any coke accumulated during the catalytic upgrading procedure. For catalyst regeneration, first all produced hydrocarbon gas and liquids are evacuated from catalytic upgrading unit 104. Nitrogen in addition to or alternative to inert gas can be used as optional carrier gas to evacuate products from catalytic upgrading unit 104 at a gas hourly space velocity (GHSV) between about 10 h$^{-1}$ to about 100 h$^{-1}$. Next, air in addition to or alternative to oxygen is introduced into catalytic upgrading unit 104 via line 124 at a GHSV at between about 10 h$^{-1}$ to about 100 h$^{-1}$. With air in place, the temperature of catalytic upgrading unit 104 is increased to between about 650° C. to about 750° C. for between about 3 hours to about 5 hours. Gas produced in part from combustion during catalyst regeneration in catalytic upgrading unit 104 can be analyzed by an in-line gas analyzer to detect the carbon dioxide concertation produced from air-atmosphere re-generation of catalyst. Oxygen in addition to or alternative to air can be supplied for catalyst regenerations via line 124.

When carbon dioxide concentration in catalytic upgrading unit 104 is reduced to less than about 0.05 vol. % to about 0.1 vol. %, the temperature of the reactor is reduced from between about 650° C. to about 750° C. to about 600° C. While the reactor temperature is decreasing to about 600° C., air in addition to or alternative to oxygen flow in line 124 is stopped. Before reintroducing additional heavy vacuum residue or heavy vacuum gas oil feed with cracking catalyst, nitrogen in addition to or alternative to another inert gas can be optionally used to evacuate air from catalytic upgrading unit 104 for between about 5 minutes to about 30 minutes. After catalyst regeneration, another catalytic upgrading cycle can begin for upgrading heavy vacuum residue in addition to or alternative to heavy vacuum gas oil to produce distillate fractions and olefins.

Gas-liquid separator unit 106 separates liquid products and gas products generated in catalytic upgrading unit 104. Gas-liquid separator unit 106 in some embodiments operates at a temperature less than about 15° C. to ensure pentane and greater molecular weight hydrocarbon molecules are liquefied and collected. Produced gases to be separated include hydrogen, methane, ethane, ethylene, propane, propylene, butanes, butenes, and other gases. Produced and separated gases are sent to a gas plant for further separation via line 126. Upgraded distillate fraction liquids are sent to a distillation unit via line 128 for further processing. Gas-liquid separator unit 106 can include any one of or any combination of two-phase separators, whether vertical or horizontal. The separation of gas and liquid depends, in part, on the cooling temperature of the separator to achieve the desired product separation. In certain applications, less than about 15° C. is preferred.

Example 1. A catalytic upgrading process similar to that described with respect to FIG. 1 was used to upgrade a vacuum residue comprising DMO with an American Petroleum Institute (API) gravity of 14.6. DMO comprises about 65 wt. % heavy residue with a boiling point above about 1050° F. as shown by simulated distillation analysis (SIMDIS) in Table 1. Generally, the boiling range for HVGO is between about 650° F. to about 1120° F., the boiling range for DAO is between about 737° F. to about 1300° F., and the boiling range for DMO is between about 800° F. to about 1350° F. A catalytic upgrading unit was utilized to upgrade de-metalized oil of vacuum residue by mixing the de-metalized oil with a straight run naphtha used as a cracking additive. Straight run naphtha was mixed with DAO, the amount of straight run naphtha being 20 wt. % of the mixed DMO and straight run naphtha, prior to the upgrading process.

Extruded ZSM-5 zeolite with 40 wt. % alumina binder was loaded into a catalytic upgrading reactor. The silica source used to synthesize ZSM-5 was tetraethylorthosilicate, and tetrapropylammonium hydroxide was the template which led to forming crystals having a size of between about 150 nm to about 350 nm. A fixed bed reactor in the catalytic upgrading unit was operated at about 600° C. during the catalytic upgrading step. The DMO feed was pre-heated to about 100° C. and was introduced to the catalytic upgrading unit at a LHSV of 1 h$^{-1}$. The catalytic upgrading process of DMO achieved high conversion and high yield of distillate fractions alongside olefin gases as shown in Table 2. The distillate fractions obtained from this upgrading reaction were produced with high yield (about 54 wt. %) and it included naphtha (16 wt. %), kerosene (8 wt. %), gas oil (8 wt. %) and fuel oil (22 wt. %). The upgrading process produced olefins at about 24 wt. %, and the propylene-to-ethylene (P:E) weight ratio was about 1:1. The olefin gases included propylene (10.6 wt. %), ethylene (9.8 wt. %), and butenes (3.4 wt. %).

TABLE 1

Distillation fractions of DMO of vacuum residue used for Example 1 catalytic upgrading process.

| Cut % | DMO feed Boiling Point, ° F. |
|---|---|
| 0 | 794.4 |
| 5 | 894 |
| 10 | 937.6 |
| 20 | 989.8 |
| 30 | 1028.9 |
| 40 | 1062.2 |
| 50 | 1094.3 |
| 60 | 1127.3 |
| 70 | 1164.1 |
| 80 | 1207.8 |
| 90 | 1268.3 |
| 95 | 1306.5 |
| 100 | 1360.2 |

TABLE 2

Upgraded products from catalytic upgrading process using DMO in Example 1.

| Product | Wt. % |
|---|---|
| Naphtha | 16 |
| Kerosene | 8 |
| Diesel | 8 |
| Fuel oil % | 22 |
| H2 | 7 |
| Ethylene | 9.8 |
| Propylene | 10.6 |
| Butenes | 3.3 |
| coke | 2.5 |

| Cut % | Boiling Point, ° F. |
|---|---|
| IBP | 151.4 |
| 5 | 206.5 |
| 10 | 250.9 |
| 20 | 309.7 |
| 30 | 358.7 |
| 40 | 453.4 |
| 50 | 554 |
| 60 | 645.3 |
| 70 | 733.1 |
| 80 | 822.4 |
| 90 | 924.9 |
| 95 | 995.6 |
| FBP | 1171.1 |

Example 2. According to the results of Example 1, the naphtha fraction produced from the catalytic upgrading process of DMO was analyzed to measure aromatic content. The obtained product included 79 wt. % naphtha, 10.7 wt. % iso-paraffins, 5.6 wt. % naphthenes, 3.6 wt. % paraffins, and olefins at less than 0.5 wt. %. Mono-aromatics were dominant in the naphtha fraction with BTX content in the range of about 27 wt. % of the obtained naphtha product.

Example 3. A catalytic upgrading process and similar reaction conditions to Example 1 were applied for upgrading another challenging heavy vacuum residue feedstock including paraffinic deasphalted oil (DAO). This feed had an API gravity of 21 and included 50 wt. % heavy residue having a boiling point above 1050° F. (Table 3). Straight run naphtha was mixed with DAO, the amount of straight run naphtha being 20 wt. % of the combined DAO and straight run naphtha feed, prior to the upgrading process. High conversion of DAO was achieved by the catalytic upgrading process which resulted in obtaining high yields of distillate fractions (36 wt. %) and olefins (36.2 wt. %) (Table 4). The distillate fractions of the obtained product from the upgrading reactions included 14.2 wt. % naphtha, 6.2 wt. % kerosene, 6.2 wt. % gas oil, and 10.1 wt. % fuel oil. Produced olefin gases in the product contained 16.7 wt. % propylene, 14 wt. % ethylene, and 5.5 wt. % butenes. The obtained P:E weight ratio was about 1:2.

TABLE 3

Distillation fractions of DAO of vacuum residue used for upgrading process in Example 3.

| Cut % | DAO feed Boiling Point, ° F. |
|---|---|
| 0 | 737.3 |
| 5 | 876 |
| 10 | 925 |
| 20 | 970.7 |
| 30 | 997.6 |
| 40 | 1019.6 |
| 50 | 1040.1 |
| 60 | 1061.4 |
| 70 | 1086.4 |
| 80 | 1118.1 |
| 90 | 1166.7 |
| 95 | 1207.1 |
| 100 | 1298.6 |

TABLE 4

Results for upgrading of DAO via catalytic upgrading process for Example 3.

| Product | Wt. % |
|---|---|
| Naphtha | 14.2 |
| Kerosene | 6.2 |
| Diesel | 6.2 |
| Fuel oil % | 10.1 |
| H2 | 7 |
| Ethylene | 14.0 |
| Propylene | 16.7 |
| Butanes | 5.5 |
| coke | 2.4 |

| Cut % | Boiling Point, ° F. |
|---|---|
| IBP | 146.5 |
| 5 | 200.9 |
| 10 | 243.9 |
| 20 | 292.1 |
| 30 | 324 |
| 40 | 361.9 |
| 50 | 446.4 |
| 60 | 538.6 |
| 70 | 623.2 |
| 80 | 713.1 |
| 90 | 819.9 |
| 95 | 900.3 |
| FBP | 1094 |

Example 4. The naphtha fraction produced from the catalytic upgrading process of DAO in Example 3 was analyzed to measure the aromatic content. The obtained aromatics in naphtha were at about 76 wt. % of the naphtha. The naphtha product also contained, 10.6 wt. % iso-paraffins, 5.1 wt. % naphthenes, 7.4 wt. % paraffins and less than 0.5 wt. % liquid olefins. Mono-aromatics were present in the naphtha fraction and BTX content was around 31.7 wt. % in the naphtha fraction, which suggest that the Research Octane Number (RON) of naphtha is greater than 91.

Example 5. A catalytic upgrading process with similar reaction conditions to Example 1 was utilized to upgrade heavy vacuum gas oil (HVGO) with a specific gravity of about 0.916. The SIMDIS analysis of HVGO are shown in Table 5. The catalytic upgrading unit was used to upgrade HVGO. The HVGO was mixed with straight run naphtha as a cracking additive at about 20% of the weight of the combined HVGO and straight run naphtha feed prior to the upgrading process. High conversion of HVGO was achieved delivering high yields of distillate fractions (30.7 wt. %) and olefins (37.6 wt. %) shown in Table 6. The distillate fractions obtained from this upgrading reaction included 7.7 wt. % naphtha, 4.2 wt. % kerosene, 6 wt. % gas oil, and 12.8 wt. % fuel oil. Furthermore, olefin gases included 17.9 wt. % propylene, 14.4 wt. % ethylene, and 5.3 wt. % butenes. The obtained P/E weight ratio was about 1.2.

TABLE 5

Distillation fractions of HVGO used in Example 5 catalytic upgrading process.

| Cut % | HVGO feed Boiling Point, ° F. |
|---|---|
| 0 | 557.7 |
| 5 | 646.2 |
| 10 | 686.5 |
| 20 | 734 |
| 30 | 766.5 |
| 40 | 795.5 |
| 50 | 824.6 |
| 60 | 855.1 |
| 70 | 887.8 |
| 80 | 925.9 |
| 90 | 976.7 |
| 95 | 1017.7 |
| 100 | 1118.9 |

TABLE 6

Results of upgrading HVGO via catalytic upgrading process of Example 5.

| Product | Wt. % |
|---|---|
| Naphtha RON > 100 | 7.7 |
| Kerosene | 4.2 |
| Diesel | 6.0 |
| Fuel oil % | 12.8 |
| H2 | 14 |
| Ethylene | 14.4 |
| Propylene | 17.9 |
| Butenes | 5.3 |
| coke | 1.4 |

| Cut % | Boiling Point, ° F. |
|---|---|
| IBP | 127.4 |
| 5 | 179.8 |
| 10 | 190.5 |
| 20 | 297.3 |
| 30 | 413.3 |
| 40 | 511.5 |
| 50 | 591.9 |
| 60 | 654.7 |
| 70 | 709.8 |
| 80 | 760.8 |
| 90 | 825 |
| 95 | 879.2 |
| FBP | 1077.2 |

Example 6. The naphtha fraction produced by the catalytic upgrading process of HVGO in Example 5 was analyzed to measure aromatic content obtained from cracking of inner heavy molecules from HVGO. The naphtha fraction contained aromatics at 78.8 wt. % along with 5.1 wt. % iso-paraffins, 9.4 wt. % naphthenes, 6.1 wt. % paraffins, and less than 0.5 wt. % olefins. Mono-aromatics were produced in the naphtha fraction and BTX content was 50.9 wt. % in the naphtha fraction, which suggested that the RON of naphtha is greater than 91.

The catalytic upgrading systems and processes are directed at upgrading DMO, DAO, or HVGO, or combinations thereof, to produce distillate fractions, olefins, and hydrogen gas as the main products. Heavy vacuum residue or HVGO or a combination can be mixed with a cracking additive to prepare the feed prior to catalytic upgrading reactions. The cracking additive applied in catalytic upgrading processes can comprise, consist of, or consist essentially of straight run naphtha having a total sulfur content from 0.01 wt. % to 1 wt. %, API gravity from about 40 to about 77 and a boiling point from between about 200° F. to 500° F.

In some embodiments, the cracking additive is added to a heavy vacuum residue or HVGO or mixed heavy feedstock to be at about 5 wt. % to about 30 wt. % of the weight of the total feedstock. In some embodiments, the cracking additive is added to a heavy vacuum residue or HVGO or mixed heavy feedstock to be at about 10 wt. % to 25 wt. % of the weight of the total feedstock. Catalytic upgrading of DAO, DMO, HVGO, or a combined feedstock thereof produces olefin gases with high yields of ethylene, propylene, trans-2-butene, 1-butene, isobutylene, and cis-2-butene. In some embodiments, the catalytic upgrading process produces about 20-25 wt. % olefin gas yield from DMO, about 30-38 wt. % from DAO, and about 30-38% from HVGO. In some embodiments, the catalytic upgrading process produces about 45-55 wt. % distillate fraction products from DMO, about 30-40 wt. % distillate fraction products from DAO, and about 28-40 wt. % distillate fraction products from HVGO.

In some embodiments, the catalytic upgrading process of DMO, DAO, HVGO, or combinations thereof produces between about 5-10 wt. % hydrogen gas. In some embodiments, the catalytic upgrading process of DMO, DAO, HVGO, or combinations thereof produces distillate fractions that comprise, consist of, or consist essentially of naphtha, kerosene, gas oil, and fuel oil. In some embodiments, a feed mixture for catalytic upgrading is prepared by adding a cracking additive to a vacuum residue feedstock, HVGO feedstock, or combination thereof in a thermal mixing unit at a temperature between about 60° C. to about 150° C. In some embodiments, thermal feed mixing unit stirring is applied at speed of between about 50 rpm to about 1500 rpm, preferably between about 100 rpm to about 400 rpm, to mix the cracking additive with feedstock.

In some embodiments, the catalytic upgrading process is operated at a liquid hourly space velocity (LHSV) of between about 0.1 $h^{-1}$ to about 20 $h^{-1}$ and preferably between about 0.25 $h^{-1}$ to about 5 $h^{-1}$. In some embodiments, the catalytic upgrading unit comprises a fixed bed catalytic reactor. In some embodiments, the catalytic upgrading unit is loaded with an extruded nano ZSM-5 zeolite with between about 20 wt. % to about 70 wt. % alumina binder. In some embodiments, the nano ZSM-5 zeolites should have a silica/alumina molar ratio in the range of 20 to 250. The nano-crystal size of ZSM-5 is in some embodiments in the range of between about 50 nm to about 350 nm.

In certain embodiments, nano ZSM-5 zeolite crystals are synthesized using at least one silica source such as tetraethylorthosilicate (TEOS), silica gel, colloidal silica 20 wt. %, colloidal silica 30 wt. %, colloidal silica 40 wt. %, or fumed silica. Silica gel is mixed with a template such as tetrapropylammonium hydroxide, which is important for structure formation of MFI-ZSM-5 structure as well as crystallization. In some embodiments, nano ZSM-5 zeolite crystals are made from different silica sources and are mixed before binding with alumina binder. The nano-crystal ZSM-5 mixture can prepared according to the following weight ratios, the ratios (X:Y) representing zeolite synthesized with tetraethylorthosilicate (TEOS) (X) as a silica source used with another ZSM-5 synthesized using a different silica source (Y) such as silica gel: about 1:1, about 1.25:0.75, about 1.5:0.5, or about 1.75:0.25.

In some embodiments, the catalytic upgrading unit is set at between about 545° C. to about 665° C., preferably between about 580° C. to 645° C. The upgrading process conversion cycle of vacuum residue feedstock, HVGO, or a mixture thereof is in the range of about 2-6 hours per cycle, and preferably about 3-4 hours to regenerate the catalyst. Nano-zeolite catalysts can be regenerated from coke by passing air over the catalyst and increasing the reactor temperature to between about 650° C. to about 750° C. for between about 3 hours to about 5 hours.

In some embodiments, the catalytic upgrading process applies low catalyst to oil (heavy feed+cracking additive) weight ratios from about 0.5:2 to about 0.5:24, per one process conversion cycle. Applying catalytic upgrading systems and processes disclosed here, DMO, DAO, heavy vacuum gas oil, and mixtures thereof can be upgraded to produce olefins at about 25-40 wt. % of a hydrocarbon product and distillate fractions at about 35-55 wt. % of a hydrocarbon product. The catalytic upgrading systems and processes apply pyrolysis that doesn't require the use of steam or hydrogen. Nano-zeolite catalysts and a fixed bed reactor allow for longer catalytic cracking cycles than conventional FCC.

The term "about" when used with respect to a value or range refers to values including plus and minus 5% of the given value or range.

The singular forms "a," "an," and "the" include plural referents, unless the context clearly dictates otherwise.

In the drawings and specification, there have been disclosed embodiments of systems and methods with a cracking additive and nano-zeolite catalyst to catalytically upgrade a heavy vacuum residue in addition to or alternative to a heavy vacuum gas oil, and although specific terms are employed, the terms are used in a descriptive sense only and not for purposes of limitation. The embodiments of the present disclosure have been described in considerable detail with specific reference to these illustrated embodiments. It will be apparent, however, that various modifications and changes can be made within the spirit and scope of the disclosure as described in the foregoing specification, and such modifications and changes are to be considered equivalents and part of this disclosure.

What is claimed is:

1. A method for upgrading a heavy oil feed to a light product comprising distillate fractions and olefins, the method comprising the steps of:
    combining a heavy oil feed with a naphtha-based cracking additive to produce a mixed heavy oil feed;
    heating the mixed heavy oil feed with a nano-zeolite catalyst, where the step of heating is carried out without hydrogen addition and without steam addition, to effect catalytic upgrading of the mixed heavy oil feed to produce lighter distillate fractions and olefins in an upgraded product, the upgraded product including at least about 20 wt. % olefins; and
    separating the lighter distillate fractions from the olefins, where the nano-zeolite catalyst to mixed heavy oil feed weight ratio is between about 0.5:2 to about 0.5:24.

2. The method according to claim 1, where the heavy oil feed has an American Petroleum Institute (API) gravity between about 5 and about 22.

3. The method according to claim 1, where the heavy oil feed is selected from the group consisting of: de-asphalted oil, de-metalized oil, heavy vacuum gas oil, and combinations thereof.

4. The method according to claim 1, where the naphtha-based cracking additive comprises straight run naphtha with an API gravity from about 40 to about 77 and a boiling point range from between about 200° F. to 500° F.

5. The method according to claim 1, where the naphtha-based cracking additive includes at least one component selected from the group consisting of: straight run naphtha with a boiling point range between about 200° F. to about 400° F., and straight run kerosene with a boiling point range between about 400° F. to about 500° F.

6. The method according to claim 1, where the naphtha-based cracking additive is between about 5 wt. % to about 30 wt. % of the mixed heavy oil feed.

7. The method according to claim 1, where the naphtha-based cracking additive is between about 10 wt. % to about 25 wt. % of the mixed heavy oil feed.

8. The method according to claim 1, where the step of heating is carried out at between about 575° C. to about 650° C. for between about 2 hours to about 6 hours.

9. The method according to claim 1, where the step of heating is carried out at between about 590° C. to about 610° C. for between about 3 hours to about 4 hours.

10. The method according to claim 1, where the nano-zeolite catalyst comprises a nano ZSM-5 silica/alumina zeolite with a silica:alumina molar ratio between about 20 to about 250 with zeolite crystals sized from about 50 to about 350 nm.

11. The method according to claim 1, where the nano-zeolite catalyst comprises a nano-zeolite catalyst material of one-dimensional or three-dimensional structure with medium pores and large pores, with 10-12 atom structure, operable to uptake heavy hydrocarbon molecule components from the mixed heavy oil feed.

12. The method according to claim 1, where the lighter distillate fractions include at least one component selected from the group consisting of: naphtha, kerosene, diesel, and fuel oil.

13. The method according to claim 1, where the olefins include at least one component selected from the group consisting of: ethylene, propylene, and butenes.

14. The method according to claim 1, further comprising the step of regenerating the nano-zeolite catalyst to remove coke after the step of heating, the step of regenerating comprising heating the nano-zeolite catalyst under air at between about 650° C. to about 750° C. for between about 3 hours to about 5 hours.

15. The method according to claim 14, further comprising the step of measuring $CO_2$ content to determine completion of the step of regenerating the nano-zeolite catalyst.

16. The method according to claim 1, where the step of combining includes stirring the heavy oil feed and naphtha-based cracking additive with a stirrer at between about 50 rpm and about 1500 rpm for between about 1 hour and about 2 hours.

17. The method according to claim 1, where the upgraded product comprises between about 5-10 wt. % hydrogen gas, about 20-40 wt. % olefin gas, and about 28-55 wt. % lighter distillate fractions.

18. A system to carry out the method of claim 1, the system comprising:
- a thermal mixing unit with a stirrer to adapted for the step of combining;
- a catalytic upgrading unit in fluid communication with the thermal mixing unit and adapted for the step of heating; and
- a gas-liquid separator unit adapted for the separating step.

19. The system according to claim 18, further comprising a heated pump and a heated line between the thermal mixing unit and the catalytic upgrading unit.

20. The system according to claim 18, where the catalytic upgrading unit is in fluid communication with a nitrogen feed and an air feed for a step of regenerating the nano-zeolite catalyst to remove coke.

21. The system according to claim 18, where the catalytic upgrading unit comprises a fixed bed reactor with the nano-zeolite catalyst disposed in the fixed bed reactor.

* * * * *